United States Patent
Wong

(12)
(10) Patent No.: US 6,334,996 B1
(45) Date of Patent: *Jan. 1, 2002

(54) CHELATORS THAT PREDOMINANTELY FORM A SINGLE STEREOISOMERIC SPECIES UPON COORDINATION TO A METAL CENTER

(75) Inventor: Ernest Wong, Langley (CA)

(73) Assignee: Resolution Pharmaceuticals Inc., Mississauga (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/997,802

(22) Filed: Dec. 24, 1997

(51) Int. Cl.[7] ............................. A61K 51/00; A61M 36/14
(52) U.S. Cl. ....................... 424/1.69; 424/1.11; 424/1.65; 424/9.1; 530/300; 530/328; 530/329; 530/330; 534/14
(58) Field of Search .................................... 424/1.11, 1.65, 424/1.69, 9.1, 9.3, 9.4, 9.5, 9.6, 9.7, 9.34; 530/300, 324–330; 534/7, 10–16

(56) References Cited

U.S. PATENT DOCUMENTS

| | | | | |
|---|---|---|---|---|
| 5,480,970 A | * | 1/1996 | Pollack et al. | 530/328 |
| 5,569,745 A | * | 10/1996 | Goodbody et al. | 530/328 |
| 5,662,885 A | * | 9/1997 | Pollak et al. | 424/1.69 |
| 5,804,158 A | * | 9/1998 | Pollak | 424/1.69 |

FOREIGN PATENT DOCUMENTS

| | | |
|---|---|---|
| EP | 0 284 071 A | 9/1988 |
| WO | WO 95/22996 | 8/1995 |
| WO | WO 95/33497 | 12/1995 |
| WO | WO 96/03427 | 2/1996 |
| WO | 9603427 | * 2/1996 |
| WO | WO 96/40293 | 12/1996 |

OTHER PUBLICATIONS

S. H. Peers et al., "Imaging a Model of Colitis with RP128, a Tc–99m–Chelated Tuftsin Antagonist", Jun. 15, 1995, The Journal of Nuclear Medicine, Proceedings of 42nd Annual Meeting, vol. 36, p. 114.

Ernest Wong, et al., "Rhenium(V) and Technetium(V) Oxo Complexes of an N2N's Peptidic Chelator: Evidence of Interconversion Between the Syn and Anti Conformations", Inorg. Chem., vol. 36(25), pp. 5799–5808, Coden: INOCAJ; ISSN: 0020–1669, 1997.

* cited by examiner

Primary Examiner—Jose' G. Dees
Assistant Examiner—Dameron Jones
(74) Attorney, Agent, or Firm—Arent Fox Kintner Plotkin & Kahn PLLC

(57) ABSTRACT

The labeling of biologically important molecules via a bifunctional chelator can result in the formation of isomers or multiple species, which can have significant impact on the biological properties of the radiopharmaceutical. For receptor-based radiopharmaceuticals, the target uptake is largely dependent on the receptor binding affinity of the targeting molecule and the blood clearance of the labeled molecule, which is determined by the physical properties of both the targeting molecule and the metal chelate. Hence, the presence of isomers for the metal chelate can have significant impact on the radiopharmaceutical. Therefore, in the development of a radiopharmaceutical or metallodrug, it is necessary to separate the isomers and evaluate the biological activities of each individual isomer. It would therefore be desirable to develop chelators that predominately form only a single stereoisomeric species upon coordination to a metal center. Disclosed herein are chelators that form a mixture enriched for a single stereoisomeric species upon coordination to a metal center.

7 Claims, No Drawings

CHELATORS THAT PREDOMINANTELY FORM A SINGLE STEREOISOMERIC SPECIES UPON COORDINATION TO A METAL CENTER

TECHNICAL FIELD

This invention relates to chelators that form a mixture enriched for a single stereoisomeric species upon coordination to a metal center.

BACKGROUND OF THE INVENTION

The current interest in the radiolabeling of biologically important molecules (proteins, antibodies, and peptides) with $^{99m}$Tc stems from the desire to develop a target specific diagnostic radiopharmaceutical.[1-10] The advantages of using $^{99m}$Tc in diagnostic nuclear medicine are well known[11-15] and a number of techniques have been developed for the $^{99m}$Tc labeling of biologically important molecules.[16-20] One obvious approach is to coordinate a $^{99m}$Tc metal directly with the targeting molecule. This approach is known as the direct labeling method and it involves the use of a reducing agent to convert disulfide linkages into free thiolates, which then bind to the $^{99m}$Tc metal. A major disadvantage of this method is the lack of control over the coordination of the $^{99m}$Tc metal and the stability of the resulting metal complex. In addition, the lack of suitable or accessible coordination sites in some proteins and peptides exclude direct labeling as a viable technique. Two common alternatives to direct labeling are the final step labeling method and the pre-formed chelate approach. Both techniques involve the use of a bifunctional chelator, which provides the site of $^{99m}$Tc coordination. The difference between the two approaches lies in the order in which the $^{99m}$Tc complex is formed. In the final step labeling method, complexation occurs after the chelator has been attached onto the targeting molecule. With the pre-formed chelate method, the $^{99m}$Tc complex is initially prepared and purified before being attached to the targeting molecule. In both techniques, the bifunctional chelator must coordinate to $^{99m}$Tc to form a complex that is stable in vivo and the chelator must have an active moiety that can react with a functional group on the targeting molecule.

A number of bifunctional chelators have been used in the labeling of proteins, peptides and monoclonal antibodies.[2, 9,10,17,21-28] Depending on the chelator, the labeling of biologically important molecules with bifunctional chelators often results in the formation of multiple species and/or isomeric complexes. An example is the $^{99m}$Tc labeling of molecules using the hydrazinonicotinamide (HYNIC) system. Since the HYNIC group can only occupy one or two sites of Tc coordination, co-ligand are required to complete the coordination sites. Glucoheptonate[29-30], tris(hydroxymethyl)methylglycine (tricine)[25], ethylenediamine-N, N'-diacetic acid (EDDA)[9], water soluble phosphines[25] [trisodium triphenylphosphine-3,3',3''-trisulfonate (TPPTS); disodium triphenylphosphine-3,3'disulfonate (TPPDS); and sodium triphenylphosphine-3-monosulfonate (TPPMS)] and polyamino polycarboxylates[9] have all been used as co-ligand in the HYNIC system. It has been clearly shown the Tc-99m labeling of molecules via the HYNIC/co-ligand system produces multiple species, which is due to the different coordination modalities of the hydrazine moiety and the co-ligands. The number of species, the type, the stability and the properties of the species vary greatly from one co-ligand to another. In the labeling of chemotatic peptide using the HYNIC system, the nature of the co-ligand also greatly affects the biodistribution of the labeled peptide.[31]

Another example of a bifunctional chelator producing multiple species is dithiosemicarbazone (DTS) system. It has been shown that the DTS bifunctional chelator produces at least four complexes with technetium.[32] Two of the complexes are known to be charged; hence they have different biodistribution from the uncharged species.

As in the development of a pharmaceutical based on organic molecules, the stereochemistry or isomerism of a metal complex is also very important in the development of a radiopharmaceutical or metallodrug. It is well known that isomers can often have different lipophilicities, biodistribution and biological activities. An example of this is the $^{99m}$Tc complex of 3,6,6,9-tetramethyl-4,8-diazaundecane-2,10-dione dioxime ($^{99m}$Tc-d,1-HMPAO or Ceretec), which is a cerebral perfusion imaging agent.[14,33-35] Though $^{99m}$Tc-d, 1-HMPAO is active, it has been shown that the meso analogs of the $^{99m}$Tc HM-PAO[14,36] complex and the $^{99m}$Tc complex of 3,3,9,9-tetramethyl-4,8-diazaundecane-2,10-dione dioxime[14,37] (PnAO) does not possess the properties necessary for use as a cerebral perfusion imaging agent.

A type of Tc and Re coordination modality common in Tc and Re radiopharmaceuticals is the coordination of a tetradentate $N_{4-x}S_x$ chelator to a metal oxo moiety to form a square pyramidal or octahedral metal oxo complex. A host of bifunctional chelators have been developed based on the tetradentate $N_{4-x}S_x$ coordination motif. Examples include $N_4$ propylene amine oxime[38], $N_3S$ triamide thiols[9, 39-43], $N_2S_2$ diamide dithiols[9, 44-46], $N_2S_2$ monoamide monoaminedithiols[47-49] and $N_2S_2$ diamine dithiols[50-55]. Functionalization of the chelator backbone enable these chelators to be attached to biologically interesting molecules. The labeling of these bifnctional chelators with $TcO^{3+}$ or $ReO^{3+}$ often produce isomers or epimers.[39-43, 46-55] The isomers or epimers (syn and anti) arise from the configuration of the metal oxo group relative to the functional group on the chelator backbone. It has been clearly shown that the biodistribution and biological activity of the syn and anti isomers are often different.[39-43, 46, 56] The Tc complex of mercaptoacetylglycylglycylglycine ($MAG_3$), a renal imaging agent, exists in the syn and anti isomers. The biological activities of the syn and anti isomers are known to be different.[39,40] The syn and anti isomers of the Tc complex of 2,3-bis(mercaptoacetamide)propanoate (map) was also shown to have different biological activity.[46] It was reported that in humans, 58% of the syn isomers was excreted at 30 minutes as compared to only 19% of the anti isomer. Another example of the isomers exhibiting a difference in biological behaviour is the $^{99m}$Tc labeled diamino dithiol piperidine conjugate, which were investigated as a brain perfusion imaging agents. It was shown that the two isomeric complexes exhibit widely disparate brain uptake.[55] At 2 minute post-administration in rats, uptake of the anti isomer in the brain was 1.08% dose/g, while the uptake of the syn isomer was 2.34% dose/g. The brain/blood ratio at 2 minute post-administration was 2.09 for the anti isomer and 5.91 for the syn isomer.

The peptide dimethylglycine-serine-cysteine-glycine is a bifunctional chelator that can be use to label biologically important molecules.[61,62] It has been shown that dimethylglycine-serine-cysteine-glycine coordinates to $TcO^{3+}$ and $ReO^{3+}$ via a monoamine diamide monothiol coordination modality.[61] The resulting Tc and Re complexes exist as two isomers; the serine $CH_2OH$ side chain is in the syn and anti conformations with respect to the metal oxo bond. The presence of the syn and anti isomers are very evident from the NMR spectral data. In the $^1$H NMR spectrum of the Re complex, there were two pairs of singlets associated with the nonequivalent methyl groups in the dimethylglycine residue. Each pair of singlets corresponded to either the syn or anti isomers. The $^1$H and $^{13}$C NMR spectral data for the Re oxo complex of dimethylglycine-sercine-cysteine-glycine-NH$_2$ (RP294) were obtained. The presence of the two isomers are clearly evident from the NMR data. In the coordination of dimethylglycine-isoleucine-cysteine-glycine (RP349) to ReO$^{3+}$, two isomers (syn and anti) were also observed. The $^{99m}$Tc labeling of RP294 and RP349 produced syn and anti isomers; two peaks were observed in the HPLC using the radiometric detector. The $^{99m}$Tc labeling of biotin with dimethylglycine-lysine-cysteine-NH$_2$ (RP332) also produced syn and anti isomers; two peaks were observed in the HPLC. These results are consistent with the coordination of other tetradentate $N_{4-x}S_x$ chelators to TcO$^{3+}$ and ReO$^{3+}$.[9,39-55]

The labeling of biologically important molecules via a bifunctional chelator can result in the formation of isomers or multiple species, which can have significant impact on the biological properties of the radiopharmaceutical. For receptor-based radiopharmaceuticals, the target uptake is largely dependent on the receptor binding affinity of the targeting molecule and the blood clearance of the labeled molecule, which is determined by the physical properties of both the targeting molecule and the metal chelate. Hence, the presence of isomers for the metal chelate can have significant impact on the radiopharmaceutical. Therefore, in the development of a radiopharmaceutical or metallodrug, it is necessary to separate the isomers and evaluate the biological activities of each individual isomer. It would therefore be desirable to develop chelators that predominately form only a single stereoisomeric species upon coordination to a metal center.

SUMMARY OF THE INVENTION

Chelators and chelator-targeting molecule conjugates are provided that form a mixture enriched for a single stereoisomeric species upon coordination to a metal center.

According to an aspect of the invention, there is provided a chirally pure compound of the formula I:

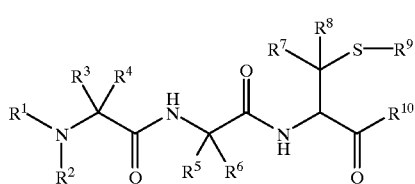

(I)

wherein
  $R^1$ is a linear or branched, saturated or unsaturated $C_{1-4}$alkyl chain that is optionally interrupted by one or two heteroatoms selected from N, O and S; and is optionally substituted by one or more substituents selected from halogen, hydroxyl, amino, carboxyl, $C_{1-4}$alkyl, aryl and C(O)R$^{10}$;
  $R^2$ is H or a substituent defined by $R^1$;
  $R^1$ and $R^2$ may together form a 5- to 8-membered saturated or unsaturated heterocyclic ring optionally substituted by one or more substituents selected from halogen, hydroxyl, amino, carboxyl, oxo, $C_{1-4}$alkyl, aryl and C(O)R$^{10}$;
  $R^3$, $R^4$ and $R^5$ are selected independently from H; carboxyl; $C_{1-4}$alkyl; $C_{1-4}$alkyl substituted with a substituent selected from hydroxyl, amino, sulfhydryl, halogen, carboxyl, $C_{1-4}$alkoxycarbonyl and aminocarbonyl; an alpha carbon side chain of a D- or L-amino acid other than proline; and C(O)R$^{10}$;
  $R^6$ is an optionally substituted 3- to 6-membered heterocylic or carbocylic ring;

or $R^6$ is

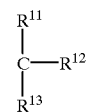

wherein $R^{11}$, $R^{12}$ and $R^{13}$ are independently selected from H, linear or branched, saturated or unsaturated $C_{1-6}$alkyl chain that is optionally interrupted by one or two heteroatoms selected from N, O and S; and is optionally substituted by one or more substituents; alkoxycarbonyl, aminocarbonyl, alkoxy, an optionally subsituted 3- to 6-membered heterocylic or carbocylic ring; with the proviso that a least one of $R^{11}$, $R^{12}$ and $R^{13}$ is not H;

or $R^6$ is

wherein $R^{14}$ and $R^{15}$ are independently selected from H, linear or branched, saturated or unsaturated $C_{1-6}$alkyl chain that is optionally interrupted by one or two heteroatoms selected from N, O and S; and is optionally substituted by one or more substituents; alkoxycarbonyl, aminocarbonyl, alkoxy, an optionally subsituted 3- to 6-membered heterocylic or carbocylic ring; with the proviso that a least one of $R^{14}$ and $R^{15}$ is not H;

or $R^6$ is

wherein X is selected from O or S and $R^{16}$ is selected from linear or branched, saturated or unsaturated $C_{1-6}$alkyl chain that is optionally interrupted by one or two heteroatoms selected from N, O and S; and is optionally substituted by one or more substituents; alkoxycarbonyl, aminocarbonyl, alkoxy, and an optionally subsituted 3- to 6-membered heterocylic or carbocylic ring;

$R^7$ and $R^8$ are selected independently from H; carboxyl; amino; $C_{1-4}$alkyl; $C_{1-4}$alkyl substituted by a substituent selected from hydroxyl, carboxyl and amino; and C(O)R$^{10}$;
  $R^9$ is selected from H and a sulfur protecting group; and
  $R^{10}$ is selected from hydroxyl, alkoxy, an amino acid residue, a linking group and a targeting molecule.

According to another aspect of the invention, there is provided a chirally pure compound of the formula II:

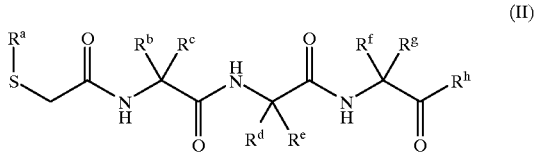
(II)

wherein
- $R^a$ is selected from H and a sulfur protecting group;
- $R^b$, $R^c$ $R^d$, $R^f$ and $R^g$ are selected independently from H; carboxyl; $C_{1-4}$alkyl; $C_{1-4}$alkyl substituted with a substituent selected from hydroxyl, amino, sulfhydryl, halogen, carboxyl, $C_{1-4}$alkoxycarbonyl and aminocarbonyl; an alpha carbon side chain of a D- or L-amino acid other than proline; and $C(O)R^h$;
- $R^e$ is an optionally subsituted 3- to 6-membered heterocylic or carbocylic ring;

or $R^e$ is

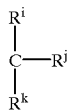

wherein $R^i$, $R^j$ and $R^k$ are independently selected from H, linear or branched, saturated or unsaturated $C_{1-6}$alkyl chain that is optionally interrupted by one or two heteroatoms selected from N, O and S; and is optionally substituted by one or more substituents; alkoxycarbonyl, aminocarbonyl, alkoxy, an optionally subsituted 3- to 6-membered heterocylic or carbocylic ring; with the proviso that a least one of $R^i$, $R^j$ and $R^k$ is not H;

or $R^e$ is

wherein $R^l$ and $R^m$ are independently selected from H, linear or branched, saturated or unsaturated $C_{1-6}$alkyl chain that is optionally interrupted by one or two heteroatoms selected from N, O and S; and is optionally substituted by one or more substituents; alkoxycarbonyl, aminocarbonyl, alkoxy, an optionally subsituted 3- to 6-membered heterocyclic or carbocylic ring; with the proviso that a least one of $R^l$ and $R^m$ is not H;

or $R^e$ is

wherein X is selected from O or S and $R^n$ is selected from linear or branched, saturated or unsaturated $C_{1-6}$-alkyl chain that is optionally interrupted by one or two heteroatoms selected from N, O and S; and is optionally substituted by one or more substituents; alkoxycarbonyl, aminocarbonyl, alkoxy, and an optionally subsituted 3- to 6-membered heterocylic or carbocylic ring; and

- $R^h$ is selected from hydroxyl, alkoxy, an amino acid residue, a linking group and a targeting molecule.

According to another aspect of the invention, the chelator-targeting molecule conjugates are provided in combination with a diagnostically useful metal or an oxide or nitride thereof.

According to another aspect of the present invention, there is provided a method of imaging a site of diagnostic interest, comprising the step of administering a diagnostically effective amount of a composition comprising a chelator-targeting molecule conjugate which is complexed to a diagnostically useful metal or an oxide or nitride thereof.

DETAILED DESCRIPTION OF THE INVENTION

In the coordination of dimethylglycine-t-butylglycine-cysteine-glycine [SEQ ID NO:1] to $TcO^{3+}$ and $ReO^{3+}$, an single isomer was observed. A single pair of singlets associated with the methyl groups in the dimethylglycine residue was observed. The $^1H$ and $^{13}C$ NMR spectral data for the Re oxo complex of dimethylglycine-L-t-butylglycine-L-cysteine-glycine [SEQ ID NO:2]. The $^{99m}Tc$ labeling of dimethylglycine-L-t-butylglycine-L-cysteine-glycine [SEQ ID NO:2] (RP455) and of dimethylglycine-D-t-butylglycine-L-cysteine-glycine [SEQ ID NO:3] (RP505) produced a single peak as observed in the HPLC using the radiometric detector. This was an unexpected result and is in contrast with what is observed in the Tc and Re oxo complexes of other tetradentate $N_{4-x}S_x$ chelators,[9, 39-55] which exist as the syn and anti isomers.

The presence of a sterically bulky group in the side chain of the peptidic chelator cause the formation of a single isomeric metal complex. In the cases of dimethylglycine-lysine-cysteine and dimethylglycine-serine-cysteine-glycine, [SEQ ID NO:6] there are insufficient bulk to cause one isomer to be preferred over another; hence the ratio of the syn and anti isomers is approximately 1:1. In the case of dimethylglycine-isoleucine-cysteine, a more sterically bulky $CH(CH_3)$—$CH_2$—$CH_3$ group was introduced into the peptidic backbone. This additional bulk caused the ratio of the syn and anti isomers to be 3:1; hence, one isomer was more favored over the other. In the case of dimethylglycine-t-butylglycine-cysteine-glycine, [SEQ ID NO:1] the incorporation of the $C(CH_3)_3$ group introduced sufficient bulk into the peptide to cause one of the isomer to be completely favored over the other; hence, a single isomeric metal complex was observed.

Molecular modeling using Quanta Charm of the Re complexes of these peptides is in agreement with the experimental results. Molecular modeling of the Re complex of dimethyglycine-L-serine-L-cysteine-glycine [SEQ ID NO:4] show the two isomers possessing thermodynamic potential energies of −67.02 and −68.37 kcal/mole. There is only a small difference in the energy of the two isomers. There is no preferred isomer for the Re complex and both the syn and anti isomers are observed at an approximate ratio of 1:1. Molecular modeling of the Re complex of dimethylglycine-lysine-cysteine shows a difference between in the thermodynamic potential energies of the two isomers to be approximately 1 kcal/mole. There is only again a small difference in the energy of the two isomers; hence both the syn and anti isomers should be observed.

In the case of dimethylglycine-L-isoleucine-L-cysteine-glycine, [SEQ ID NO:5] a more bulky side chain is incorporated into the peptidic backbone. Molecular modeling of the Re complex of the dimethylglycine-isoleucine-cysteine-glycine [SEQ ID NO:12] show one of the isomer having a potential energy that is approximately 3 kcal/mole lower than the energy of the other isomer. There is a now a greater difference in the energies and there is a slight preference for one isomer over the other. Hence, the ratio of the two isomers is 3:1.

In the case of dimethylglycine-L-t-butylglycine-L-cysteine-glycine, [SEQ ID NO:2] molecular modeling of the Re complex shows the difference in the potential energies of the two isomers to be approximately 6.5 kcal/mole. With the Re complex of dimethylglycine-D-t-butylglycine-L-cysteine-glycine, [SEQ ID NO:3] the difference in the energies of the two isomers is about 8.5 kcal/mole. One isomer is significantly preferred over the other; hence, only a single isomer is observed for the Re and Tc complexes. Molecular modeling of the Re complex of mercaptoacetyl-t-butylglycine-glycine-glycine shows that the syn and anti isomers of the complex with a energy difference of 7.4. The metal complexes of mercaptoacetyl-t-butylglycine-glycine-glycine preferred one isomer over the other and should exist as a single isomer.

Artificial amino acids with bulky side chains can be prepared according to known literature methods.63-67 For example, both L- and D-amino acid derivatives can be prepared starting directly from the commercially available L- or D-serine, respectively.[67] Using this method, alkyl, phenyl and other bulky groups can be incorporated into serine to produce β-hydroxy-α-amino acids.[67] Hence, artificial amino acids with bulky side chains can be incorporated into peptidic chelators, which would produce a single species and an single isomeric metal complex.

The advantage of having a bifunctional chelator that forms a single isomeric metal complex is that in the labeling of biologically important molecule, there is only a single radiolabeled species. Hence, there is no need to isolate and evaluate the biological activity and toxicity of multiple compounds. It is also easier to formulate a radiopharmaceutical kit that consistently produces a single radiolabeled compound than one that produces a series of radiolabeled compounds. In the labeling of a biologically important molecule with a chelator that results in multiple species, there is a necessity to formulate the kit such that the labeling consistently produce the same set of compounds in the same ratio. This is eliminated with the use of a chelator that produces a single metal complex. Quality control of a radiopharmaceutical is also simplified by the use of a chelator that result in a single species as it is much easier to develop a quality control protocol that identifies a single well characterized compound than one that have to identify the presence and quantity of multiple compounds.

An addition benefit from the incorporation of different side chain groups into the peptidic chelator backbone to cause a single isomer is that the lipophilicity of the resulting metal complexes is altered by the addition of the different groups. The log D of the $^{99m}$Tc complex of dimethylglycine-t-butylglycine-cysteine-glycine [SEQ ID NO:1] is −1.3, compared to −2.3 for the $^{99m}$Tc complex of dimethylglycine-serine-cysteine-glycine.[SEQ ID NO:6]

The terms defining the variables $R^1$–$R^{10}$, $R^a$–$R^n$ and X as used hereinabove in formula (I) have the following meanings:

"alkyl" refers to a straight or branched $C_1$–$C_8$ chain and includes lower $C_1$–$C_4$ alkyl;

"alkoxy" refers to straight or branched $C_1$–$C_8$ alkoxy and includes lower $C_1$–$C_4$ alkoxy;

"thiol" refers to a sulfhydryl group that may be substituted with an alkyl group to form a thioether;

"sulfur protecting group" refers to a chemical group that is bonded to a sulfur atom and inhibits oxidation of sulfur and includes groups that are cleaved upon chelation of the metal. Suitable sulfur protecting groups include known alkyl, aryl, acyl, alkanoyl, aryloyl, mercaptoacyl and organothio groups.

"Linking group" refers to a chemical group that serves to couple the targeting molecule to the chelator while not adversely affecting either the targetting function of the peptide or the metal binding function of the chelator. Suitable linking groups include alkyl chains; alkyl chains optionally substituted with one or more substituents and in which one or more carbon atoms are optionally replaced with nitrogen, oxygen or sulfur atoms. Other suitable linking groups include those having the formula $A^1$—$A^2$—$A^3$ wherein $A^1$ and $A^3$ are independently selected from N, O and S; and $A^2$ includes alkyl optionally substituted with one or more substituents and in which one or more carbon atoms are optionally replaced with nitrogen, oxygen or sulfur atoms; aryl optionally substituted with one or more substituents; and heteroaryl optionally substituted with one or more substituents. Still other suitable lining groups include amino acids and amino acid chains functionalized with one or more reactive groups for coupling to the glycopeptide and/or chelator. In one embodiment, the linking group is a peptide of 1 to 5 amino acids and includes, for example, chains of 1 or more synthetic amino acid residues such as β-Alanine residues. In another embodiment, the linking group is NH-alkyl-NH.

"Targeting molecule" refers to a molecule that can selectively deliver a chelated radionuclide or MRI contrasting agent to a desired location in a mammal. Preferred targeting molecules selectively target cellular receptors, transport systems, enzymes, glycoproteins and processes such as fluid pooling. Examples of targeting molecules suitable for coupling to the chelator include, but are not limited to, steroids, proteins, peptides, antibodies, nucleotides and saccharides. Preferred targeting molecules include proteins and peptides, particularly those capable of binding with specificity to cell surface receptors characteristic of a particular pathology. For instance, disease states associated with over-expression of particular protein receptors can be imaged by labeling that protein or a receptor binding fragment thereof coupled to a chelator of invention. Most preferably targeting molecules are peptides capable of specifically binding to target sites and have three or more amino acid residues. The targeting moiety can be synthesised either on a solid support or in solution and is coupled to the next portion of the chelator-targeting moiety conjugates using known chemistry.

Chelator conjugates of the invention may be prepared by various methods depending upon the chelator chosen. The peptide portion of the conjugate if present is most conveniently prepared by techniques generally established in the art of peptide synthesis, such as the solid-phase approach. Solid-phase synthesis involves the stepwise addition of amino acid residues to a growing peptide chain that is linked to an insoluble support or matrix, such as polystyrene. The C-terminus residue of the peptide is first anchored to a commercially available support with its amino group protected with an N-protecting agent such as a t-butyloxycarbonyl group (tBoc) or a fluorenylmethoxycarbonyl (FMOC) group. The amino protecting group is removed with suitable deprotecting agents such as TFA in the case of tBOC or piperidine for FMOC and the next amino acid residue (in N-protected form) is added with a coupling agent such as dicyclocarboimide (DCC). Upon formation of a peptide bond, the reagents are washed from the support. After addition of the final residue, the peptide is cleaved from the support with a suitable reagent such as trifluoroacetic acid (TFA) or hydrogen fluoride (HF).

Conjugates may further incorporate a linking group component that serves to couple the peptide to the chelator while not adversely affecting either the targetting function of the peptide or the metal binding function of the chelator.

In accordance with one aspect of the invention, chelator conjugates incorporate a diagnostically useful metal capable of forming a complex. Suitable metals include radionuclides such as technetium and rhenium in their various forms such as $^{99m}TcO^{3+}$, $^{99m}TcO_2^+$, $ReO^{3+}$ and $ReO_2^+$. Incorporation of the metal within the conjugate can be achieved by various methods common in the art of coordination chemistry. When the metal is technetium-99m, the following general procedure may be used to form a technetium complex. A peptide-chelator conjugate solution is formed initially by dissolving the conjugate in aqueous alcohol such as ethanol. The solution is then degassed to remove oxygen then thiol protecting groups are removed with a suitable reagent, for example with sodium hydroxide and then neutralized with an organic acid such as acetic acid (pH 6.0–6.5). In the labelling step, a stoichiometric excess of sodium pertechnetate, obtained from a molybdenum generator, is added to a solution of the conjugate with an amount of a reducing agent such as stannous chloride sufficient to reduce technetium and heated. The labelled conjugate may be separated from contaminants $^{99m}TcO_4^-$ and colloidal $^{99m}TcO_2$ chromatographically, for example with a C-18 Sep Pak cartridge.

In an alternative method, labelling can be accomplished by a transchelation reaction. The technetium source is a solution of technetium complexed with labile ligands facilitating ligand exchange with the selected chelator. Suitable ligands for transchelation include tartarate, citrate and heptagluconate. In this instance the preferred reducing reagent is sodium dithionite. It will be appreciated that the conjugate may be labelled using the techniques described above, or alternatively the chelator itself may be labelled and subsequently coupled to the peptide to form the conjugate; a process referred to as the "prelabelled ligand" method.

Another approach for labelling conjugates of the present invention involves techniques described in a co-pending U.S. application Ser. No. 08/152,680 filed Nov. 16, 1993, incorporated herein by reference. Briefly, the chelator conjugates are immobilized on a solid-phase support through a linkage that is cleaved upon metal chelation. This is achieved when the chelator is coupled to a functional group of the support by one of the complexing atoms. Preferably, a complexing sulfur atom is coupled to the support which is functionalized with a sulfur protecting group such as maleimide.

When labelled with a diagnostically useful metal, chelator conjugates of the present invention can be used to detect sites of inflammation by procedures established in the art of diagnostic imaging. A conjugate labelled with a radionuclide metal such as technetium-99m may be administered to a mammal by intravenous injection in a pharmaceutically acceptable solution such as isotonic saline. The amount of labelled conjugate appropriate for administration is dependent upon the distribution profile of the chosen conjugate in the sense that a rapidly cleared conjugate may be administered in higher doses than one that clears less rapidly. Unit doses acceptable for imaging inflammation are in the range of about 5–40 mCi for a 70 kg individual. In vivo distribution and localization is tracked by standard scintigraphic techniques at an appropriate time subsequent to administration; typically between 30 minutes and 180 minutes depending upon the rate of accumulation at the target site with respect to the rate of clearance at non-target tissue.

| List of Abbreviations | |
|---|---|
| Abbreviation | Description |
| Acm | acetoamidomethyl |
| Ar | argon |
| Arg | arginine |
| Boc | tert-butyloxycarbonyl |
| Cys | cysteine |
| DIEA | diisopropylethylamine |
| Dimethylgly | N,N-dimethylglycine |
| DMF | N,N-dimethylformamide |
| ES-MS | Electron Spray Mass Spectrometry |
| Fmoc | 9-fluorenylmethyloxycarbonyl |
| Gly | glycine |
| HBTU | 2-(1H-benzotriazol-1-yl)-1,1,3,3-tetramethyl-uronium hexafluorophosphate |
| HOBT | 1-hydroxybenzotriazole |
| HPLC | high performance liquid chromatography |
| Ile | isoleucine |
| Leu | leucine |
| Lys | lysine |
| mL | millilitre(s) |
| mmol | millimole(s) |
| mol | mole(s) |
| Mott | 4-methoxytrityl |
| NaOH | sodium hydroxide |
| NMP | N-methylpyrrolidone |
| Phe | phenylalanine |
| Pmc | 2,2,5,7,8-pentamethylchroman-6-sulfonyl |
| $R_t$ | retention time |
| sasrin | 2-methoxy-4-alkoxybenzyl alcohol (super acid sensitive resin) |
| Ser | serine |
| t-Bu | tert-butyl |
| TFA | trifluoroacetic acid |
| Thr | threonine |
| Trt | trityl |
| Tyr | tyrosine |
| $Y^e$-R | protection group R is attached to the peptide chain via the atom, Y, on the amino acid side chain (Y is N, O or S and R is Acm, Boc, Mott, t-Bu or Trt) |

Experimental Section

Materials. N-methylpyrrolidone, N,N-dimethylformamide, 100 mmol 2-(1H-benzotriazol-1-yl)-1,1,3,3-tetramethyl-uronium hexafluorophosphate/0.5M 1-hydroxybenzotriazole DMF, 2.0M diisopropylethylamine/NMP, dichloromethane and trifluoroacetic acid were purchased from Applied Biosystems Inc. Triethylamine and tert-butyl methyl ether were purchased from Aldrich Chemical Inc. Fmoc amino acid derivatives and Fmoc-Gly sasrin resin was purchased from Bachem Bioscience Inc. All chemicals were used as received. [ReO$_2$(en)$_2$]Cl was prepared according to literature methods.[57,58]

Instrumentation. NMR spectra were recorded on a Bruker AC-300 and on a Bruker DRX-500 NMR spectrometer and are reported as δ in ppm from external TMS. Mass spectra (electrospray) were obtained on a Sciex API#3 mass spectrometer in the positive ion detection mode. HPLC analyses and purifications were made on a Beckman System Nouveau Gold chromatographic system with a Waters 4 mm radial pak C-18 column. During analytical HPLC analysis, the mobile phase was changed from 100% 0.1% aqueous trifluoroacetic acid to 100% acetonitrile containing 0.1% trifluoroacetic acid over 20 minutes at a flow rate of 2 mL/min. All HPLC analyses were monitored with a UV detector set at 214 and 254 nm. Solid phase peptide syntheses were performed on an ABI Peptide Synthesizer model 433A using FastMoc chemistry and preloaded Fmoc amino acid sasrin resin.[59,60] Molecular modeling of the Re complexes was performed using Quanta Charm version 3.3.[63] HPLC analyses of the $^{99m}Tc$ samples were made on a Beckman System Gold chromatographic system with a Vydac 4.6 mm radial pak C-18 column. The mobile phase was changed from 100% water containing 0.1% trifluoroacetic acid to 70% acetonitrile containing 0.1% trifluoroacetic acid over 25 minutes at a flow rate of 1 mL/min. The HPLC analyses of the $^{99m}$Tc samples were monitored with a UV detector set at 215 nm and a radiometric gamma detector.

Synthesis of Peptides. Peptides of various amino acid sequences were prepared via a solid phase peptide synthesis method on an automated peptide synthesizer using FastMoc 1.0 mmole chemistry.[59,60] Preloaded Fmoc amino acid sasrin resin and Fmoc amino acid derivatives were used. Prior to the addition of each amino acid residue to the N-terminus of the peptide chain, the FMOC group was removed with 20% piperidine in NMP. Each Fmoc amino acid residue was activated with 0.50 M HBTU/HOBt/DMF, in the presence of 2.0M DIEA/NMP. The C-terminus of the completed peptide was attached to the resin via the sasrin linker. The peptidyl resin was washed with dichloromethane and dried under vacuum for 20–24 hours. The peptide was cleaved off the resin by stirring the peptidyl resin in 95% aqueous trifluoroacetic acid for 3–4 hours. The sasrin resin was filtered and the filtrate was added dropwise to tert-butyl methyl ether at 0° C. The peptide precipitate out of the ether. The precipitate was collected by centrifugation and dissolved in minimal amount of water. The aqueous peptide solution was lyophilized to yield the product. The product was analyzed by mass spectrometry and by HPLC. The product was purified by HPLC. This method was used to prepare the following peptides 1) RP349: Dimethylgly-L-Ile-L-Cys(S$^\epsilon$-Acm)-Gly [SEQ ID NO:7]

2) RP332: Dimethylgly-L-lysine(N$^\epsilon$-Biotin)-L-Cys(S$^\epsilon$-Acm)

3) RP455: Dimethylgly-L-t-Butylgly-L-Cys(S$^\epsilon$-Acm)-Gly [SEQ ID NO:8]

4) RP505: Dimethylgly-D-t-Butylgly-L-Cys(S$^\epsilon$-Acm)-Gly [SEQ ID NO:9]

5) RP502: Dimnethylgly-L-t-Butylgly-L-Cys(S$^\epsilon$-Acm)-Gly-Thr-Lys-Pro-Pro-Arg [SEQ ID NO:10]

Synthesis of Re Oxo Complex of Dimethylglycine-L-t-butylgly-L-Cys-Gly: [SEQ ID NO:2] To remove the acm protecting group, dimethylgly-L-t-butylgly-L-Cys-(S$^\epsilon$-Acm)-Gly [SEQ ID NO:8] (84.0 mg, 0.187 mmoles) was dissolved in 2 mL of 30% acetic acid. Mercury(II) acetate (91.6 mg, 0.287 mmoles) was added to the solution and the solution was stirred under Ar at room temperature for 18 hours. H$_2$S gas was then bubbled through the solution for 5 minutes, causing black HgS to precipitate. The precipitate was removed by centrifugation, and the filtrate was frozen and lyophilized overnight. [ReO$_2$(en)$_2$]Cl (88.6 mg, 0.237 mmoles) was dissolved in 3 mL of distilled water and added to the lyophilized deprotected peptide. The solutions was a light green colour. The pH of the solution was adjusted to 6 using 1M NaOH. The solution was refluxed under Ar for 2 hours, during which time the solution changed from green to red. The solution was frozen and lyophilized overnight, yielding a red solid. Purification of the product was done by HPLC. Mass spectrum (electrospray): m/z=577 ([MH]$^+$, [C$_{15}$H$_{27}$N$_4$O$_6$Re$_1$S$_1$]. HPLC retention time: 9.52 min. $^1$H NMR and $^{13}$C NMR (500 MHz, D$_2$O) spectral data are shown in Table 3 and 4. Log D (pH: 7.4): −1.3.

Synthesis of Re Oxo Complex of Dimethylgly-D-t-butylgly-L-Cys-Gly: [SEQ ID NO:3] The procedure for the synthesis of the Re oxo complex of dimethylgly-D-t-butylgly-L-Cys-Gly was the same as the one described for the synthesis of the Re complex of Dimethylgly-L-t-butylgly-L-Cys-Gly. [SEQ ID NO:2] Mass spectrum (electrospray): m/z=([MH]$^+$, [C$_{15}$H$_{26}$N$_4$O$_6$Re$_1$S$_1$]. HPLC retention time: 9.62 min. $^1$H NMR (300 MHz, D$_2$O): 2.89 (s, methyl $^1$H in the dimethylglycine residue), 3.65 (s, methyl $^1$H in the dimethylglycine residue).

Synthesis of Re Oxo Complex of Dimethylgly-L-t-Butylgly-L-Cys-Gly-Thr-Lys-Pro-Pro-Arg: The procedure for the synthesis of the Re oxo complex Dimethylgly-L-t-Butylgly-L-Cys-Gly-Thr-Lys-Pro-Pro-Arg [SEQ ID NO:11] was the same as the one described for the synthesis of the Re complex of dimethylgly-L-t-butylgly-L-Cys-Gly. [SEQ ID NO:2] Mass spectrum (electrospray): m/z=1155 ([MH]$^+$, [C$_{41}$H$_{71}$N$_{13}$O$_{12}$Re$_1$S$_1$]$^+$). HPLC retention time: 8.82 min. $^1$H NMR (500 MHz, D$_2$O): 2.63 (s, methyl $^1$H in the dimethylglycine residue), 3.56 (s, methyl $^1$H in the dimethylglycine residue).

Synthesis of Re Oxo Complex of Dimethylgly-L-Ile-L-Cys-Gly: [SEQ ID NO:5] The procedure for the synthesis of the Re oxo complex Dimethylgly-L-ile-L-cys-gly [SEQ ID NO:5] was the same as the one described for the synthesis of the Re complex of dimethylgly-L-t-butylgly-L-cys-gly. [SEQ ID NO:2] Mass spectrum (electrospray): m/z=577 ([MH]$^+$, [C$_{41}$H$_{71}$N$_{13}$O$_{12}$Re$_1$S$_1$]$^+$), m/z=598 ([MH]$^+$], [C$_{41}$H$_{71}$N$_{13}$O$_{12}$Re$_1$S$_1$]$^+$). HPLC retention time: 9.50 min. $^1$H NMR (300 MHz, D$_2$O): 2.60 (s, methyl $^1$H in the dimethylglycine residue of isomer A), 2.76 (s, methyl $^1$H in the dimethylglycine residue of isomer B), 3.68 (s, methyl $^1$H in the dimethylglycine residue of isomer A), 3.72 (s, methyl $^1$H in the dimethylglycine residue of isomer B).

Synthesis of the $^{99m}$Tc complex. The peptide (0.2–0.5 μmoles) was dissolved in 200 μL of saline. Na[$^{99m}$TcO$_4$] (10 mCi) was added to the solution, followed by tin(II) chloride (7.5×10$^3$ μg, 39 μmoles), sodium gluconate (1.3×10$^3$μg, 5.8 μmoles), and 20 μL of 0.1M NaOH. The solution was left at room temperature for 1 hour or heated at 100° C. for 15 minutes. In the synthesis of the $^{99m}$Tc complex, the acetoamidomethyl protection group was displaced from the cysteine residue in RP414. The $^{99m}$Tc complex was analyzed by HPLC. The $^{99m}$Tc complexes of RP455, RP505 and RP502 was co-injected with the corresponding Re complexes. The HPLC retention times of the $^{99m}$Tc peptidic complexes are as follows:

1) $^{99m}$Tc complex of RP349 (Dimethylgly-L-Ile-L-Cys-Gly) [SEQ ID NO:5]: HPLC retention time: $^{99m}$Tc (RP349) R$_t$=19.41, 21.53 min (radiometric gamma detector).

2) $^{99m}$Tc complex of RP332 (Dimethylgly-L-lysine(N$^\epsilon$-Biotin)-L-Cys): HPLC retention time: $^{99m}$Tc(RP332) R$_t$=11.54, 11.97 min (radiometric gamma detector).

3) $^{99m}$Tc complex of RP455 (Dimethylgly-L-t-Butylgly-L-Cys-Gly) [SEQ ID NO:2]: HPLC retention time: ReO(RP455) R$_t$=21.18 min (UV detector set at 215 nm); $^{99m}$Tc(RP445) R$_t$=21.49 min (radiometric gamma detector).

4) $^{99m}$Tc complex of RP505 (Dimethylgly-D-t-Butylgly-L-Cys-Gly) [SEQ ID NO:3]: HPLC retention time: ReO(RP505) R$_t$=18.16 min (UV detector set at 215 nm); $^{99m}$Tc(RP505) R$_t$=18.89 min (radiometric gamma detector).

5) $^{99m}$Tc complex of RP502 (Dimethylgly-L-t-Butylgly-L-Cys(S$^\epsilon$-Acm)-Gly-Thr-Lys-Pro-Pro-Arg) [SEQ ID NO:10]: HPLC retention time: ReO(RP502) R$_t$=19.76 min (UV detector set at 215 mn); $^{99m}$Tc(RP502) R$_t$=20.10 min (radiometric gamma detector).

References (1) Baidoo, K. E.; Lever, S. Z. *Bioconjugate Chem.* 1990, 1, 132.
(2) Eisenhut. M.; Missfeldt, M.; Lehmann, W. D.; Karas, M. *J. Label Compound Radiopharm.* 1991, 29, 1283.
(3) Fritzberg, A. R.; Beaumier, P. L. *J. Nucl. Med.* 1992, 33, 394.
(4) Fischman, A. J.; Babich, J. W.; Strauss, H. W. *J. Nucl. Med.* 1993, 34, 2253.
(5) Thakur, M. L. *Nucl. Med. Commun.* 1995, 16, 724.
(6) Malin, R.; Steinbrecher, R.; Jannsen, J.; Semmler, W.; Noll, B.; Johannsen, B.; Frommel, C.; Hohne, W.; Schneider-mergener, J. *J. Am. Chem. Soc.* 1995, 117, 11821.
(7) Pearson, D. A.; Lister-James, J.; McBride, W. J.; Wilson, D. M.; Martel, L. J.; Civitello, E. R.; Taylor, J. E.; Moyer, B. R.; Dean, R. T. *J. Med. Chem.* 1996, 39, 1361.
(8) Lister-James, J.; Knight, L. C.; Maurer, A. H.; Bush, L. R. *J. Nucl. Med.* 1996, 37, 775.
(9) Liu, S.; Edwards, D. S.; Looby, R. J.; Harris, A. R.; Poirier, M. J.; Barrett, J. A.; Heminway, S. J.; Carroll, T. R. *Bioconjugate Chem.* 1996, 7, 63.
(10) Liu, S.; Edwards, D. S.; Looby, R. J.; Poirier, M. J.; Rajopadhye, M.; Bourque, J. P.; Carroll, T. R. *Bioconjugate Chem.* 1996, 7, 196.
(11) Deutsch, E.; Libson, K.; Jurisson, S.; Lindoy, L. F. *Prog. Inorg. Chem.* 1983, 30, 75.
(12) Melnik, M.; Van Lier, J. E. *Coord. Chem. Rev.* 1987, 77, 275.
(13) Mazzi, U. *Polyhedron,* 1989, 8, 1633.
(14) Jurisson, S.; Berning, D.; Jia, W.; Ma, D. *Chem. Rev.* 1993, 93, 1137.
(15) Tisato, F.; Refosco, F.; Bandoli, G. *Coord. Chem. Rev.* 1994, 135, 325.
(16) Otsuka, F. L.; Welch, M. J. *Nucl. Med. Biol.* 1987, 14, 243.
(17) Fritzberg, A. R.; Berninger, R. W.; Hardey, S. W.; Wester, D. W. *Pharm. Res.* 1988, 5, 325.
(18) Eckelman, W. C.; Paik, C. H.; Steigman, J. *Nucl. Med. Biol.* 1989, 16, 171.
(19) Hnatowich, D. J. *Semin. Nucl. Med.* 1990, 20, 80.
(20) Srivastava, s. C.; Mease, R. C. *Nucl. Med. Biol.* 1991, 18, 589.
(21) Liang, F. H.; Virzi, F.; Hnatowich, D. J. *Nucl. Med. Biol.* 1987, 14, 63.
(22) Chianelli, M.; Signore, A.; Fritzberg, A. R.; Mather, S. J. *Eur. J. Nucl. Med.* 1992, 19, 625.
(23) Baidoo, K. E.; Lever, S. Z.; Scheffel, U. *Bioconjugate Chem.* 1994, 5, 114.
(24) Eisenhut, M.; Lehmann, W. D.; Becker, W.; Behr, T. *J. Nucl. Med.* 1996, 37, 362.
(25) Edwards, D. S.; Liu, S.; Barrett, J. A.; Harris, A. R; Looby, R. J.; Ziegler, M. C.; Heminway, S. J.; Carroll, T. R. *Bioconjugate Chem.* 1997, 8, 146.
(26) Barrett, J. A.; Crocker, A. C.; Damphousse, D. J.; Heminway, S. J.; Liu, S.; Edwards, D. S.; Lazewatsky, J. L.; Kagun, M.; Mazaika, T. J.; Carroll, T. R. *Bioconjugate Chem.* 1997, 8, 155.
(27) Thakur, M. L.; Kolan, H.; Li, J.; Wiaderkiewicz, R.; Pallela, V. R.; Duggaraju, R.; Schally, A. V. *Nucl. Med. Biol.* 1997, 24, 105.
(28) Childs, R. L.; Hnatowich, D. J. *J. Nucl. Med.* 1985, 26, 293.
(29) Fischman, A. J.; Babich, J. W.; Rubin, H. R. *Semin. Nucl. Med.* 1993, 24, 154.
(30) Babich, J. W.; Solomon, H.; Pike, M. C.; Kroon, D.; Graham, W.; Abrams, M. J.; Tompkins, R. G.; Rubin, R. H.; Fischman, A. J. *J. Nucl. Med.* 1993, 34, 1967.
(31) Babich, J. W.; Fichman, A. J. *Nucl. Med. Biol.* 1995, 22, 25.
(32) Hosotani, T.; Yokoyama, A.; Arano, Y.; Horiuchi, K.; Wasaki, H.; Saji, H.; Torizuka, K. *Nucl. Med. Biol.* 1986, 12, 431.
(33) Leonard, J. P.; Nowotnik, D. P.; Neirinckx, R. D. *J. Nucl. Med.* 1986, 27, 1819.
(34) Neirinckx, R. D.; Canning, L. R.; Piper, I. M.; Nowotnik, d. P.; Pickett, R. D.; Holmes, R. A.; Volkert, W. A.; Forster, A. M.; Weisner, P. S.; Marriott, J. A.; Chaplin, S. B. *J. Nucl. Med.* 1987, 28, 191.
(35) Neirinckx, R. D.; Burke, J. F.; Harrison, R. C.; Forster, A. M.; Andersen, A. R.; Lassen, N. A. *J. Cereb. Blood Flow Metab.* 1988, 8, S4.
(36) Hohm, S.; Anderson, A. R.; Vorstrup, S.; Lassen, N. A.; Paulson, O. B.; Holmes, R. A.; *J. Nucl. Med.* 1985, 26, 1129.
(37) Sharp, P. F.; Smith, F. W.; Gemmell, H. G.; Lyall, D.; Evans, N. T. S.; Gvozdanovic, D.; Davidson, J.; Tyrrell, D. A.; Pickett, R. D.; Neirinckx, R. D. *J. Nucl. Med.* 1986, 27, 171
(38) Linder, K. E.; Wen, M. D.; Nowotnik, D. P.; Malley, M. F.; Gougoutas, J. Z.; Nunn, A. D.; Eckelman, W. C. *Bioconjugate Chem.* 1991, 2, 160
(39) Rao, T. N.; Adhikesavalu, D.; Camerman, A.; Fritzberg, A. R. *J. Am. Chem. Soc.* 1990, 112, 5798
(40) Eshima, D.; Taylor Jr., A.; Fritzberg, A. R.; Kasina, S.; Hansen, L.; Sorenson, J. F. *J. Nucl. Med.* 1987, 28, 1180
(41) Subhani, M.; Cleynhens, B.; Bormans, G.; Hoogmartens, M.; De Roo, M.; Verbruggen, A. M. In Technetium and Rhenium in Chemistry and Nuclear Medicine-3; Nicoline M.; Banoli, G.; Mazzi, U., Eds.; Cortina International, Verona, Italy, 1990, p. 453.
(42) Bormans, G.; Cleynhens, B.; Hoogmartens, M.; De Roo, M.; Verbruggen, A. M. In Technetium and Rhenium in Chemistry and Nuclear Medicine-3; Nicoline M.; Banoli, G.; Mazzi, U., Eds.; Cortina International, Verona, Italy, 1989, p. 661.
(43) Bormans, G.; Cleynhens, B.; Adriaens, P.; De Roo, M.; Verbruggen, A. M. *J. Labelled Compounds and Radiopharmaceuticals,* 1993, 33, 1065
(44) Lister-James, J.; Knight, L. C.; Mauer, A. H.; Bush, L. R.; Moyer, B. R.; Dean, R. T. *J. Nucl. Med.* 1996, 37, 775
(45) Muto, P.; Lastoria, S.; Varrella, E.; Salvatore, M.; Morgano, G.; Lister-James, J.; Bernardy, J. D.; Dean, R. T. Wencker, D.; Boer, J. S. *J. Nucl. Med.* 1995, 36, 1384
(46) Klingensmith III, W. C.; Fritzberg, A. R.; Spitzer, V. M.; Johnson, D. L.; Kuni, C. C.; Williamson, M. R.; Washer, G.; Weil III, R. *J. Nucl. Med.* 1984, 25, 42.
(47) Marchi, A.; Marvelli, L.; Rossi, R.; Magon, L.; Bertolasi, V.; Ferretti, V.; Gilli, P.; *J. Chem. Soc., Dalton Trans.* 1992, 1485
(48) Kung, H. F.; Bradshaw, J. E.; Chumpradit, S.; Zhang, Z. P.; Kung, M. P.; Mu, M.; Frederick, D. In Technetium and Rhenium in Chemistry and Nuclear Medicine-4; Nicoline M.; Banoli, G.; Mazzi, U., Eds.; Cortina International, Verona, Italy, 1995, p.293.
(49) Meegalla, S.; Plossl, K.; Dung, M.-P.; Chumpradit, S.; Stevenson, D. A.; Kushner, S. A.; McElgin, W. T.; Mozley, P. D.; Kung, H. F. *J. Med. Chem.* 1997, 40, 9
(50) Edwards, D. S.; Cheesman, E. H.;; Watson, M. W.; Maheu, L. J.; Nguyen, S. A.; Dimitre, L.; Nason, T.; Watson, A. D.; Walovitch, R. In Technetium and Rhenium in Chemistry and Nuclear Medicine-3; Nicoline M.; Banoli, G.; Mazzi, U., Eds.; Cortina International, Verona, Italy, 1990, p. 431.
(51) Oya, S.; Kung, M.-P.; Frederick, D.; Kung, H. F. *Nucl. Med. Biol.* 1995, 22, 749.

(52) Kung, H. F.; Guo, Y. Z.; Yu, C. C.; Billings, J.; Subramanyam, B.; Calabrese, J. C. *J. Med. Chem.* 1989, 32, 433.
(53) Mach, R. H.; Kung, H. F.; Guo, Y. Z.; Yu, C. C.; Subramanyam, V.; Calabrese, J. C. *Nucl. Med. Biol.* 1989, 16, 829.
(54) Francesconi, L. C.; Graczyk, G.; Wehrli, S.; Shaikh, S. N.; McClinton, D.; Liu, S.; Zubieta, J.; Kung, H. F. *Inorg. Chem.* 1993, 32, 3114.
(55) Efange, S. M. N.; Kung, H. F.; Billings, S. S.; Blau, M. *J. Med. Chem.* 1988, 31, 1043.
(56) Walovitch, R. C.; Cheesman, E. H.; Maheu, L. J.; Hall, K. M. *J. Cereb. Blood Flow Metab.* 1988, 8, S4.
(57) Rouschias, G. *Chem. Rev.* 1974, 74, 531.
(58) Fergusson, J. E. *Coord. Chem. Rev.* 1966, 1, 459.
(59) *User' Manual of Peptide Synthesizer Model 433A,* Applied BioSystems, Philadelphia, 1993.
(60) *Introduction to Cleavage Techniques,* Applied BioSystems, Philadelphia, 1990.
(61) Wong, E.; Fauconnier, T.; Bennett, S.; Valliant J.; Nguyen, T.; Lau, F.; Lu, L. F. L.; Pollak,; Bell, R. A.; Thornback, J. R. *Inorg. Chem.* 1997, in press.
(62) Peers, S. H.; Tran, L. L.; Eriksson, S. J.; Ballinger, J.; Goodbody, A. E. *J. Nucl. Med.* 1995,36, 114P.
(63) Williams, R. M. Synthesis of Optically Active a-Amino Acids; Pergamon: Toronto, Canca, 1987.
(64) Arnold, L. D.; May, r. G.; Vederas, J. C. *J. Am. Chem. Soc.* 1987, 109, 4649.
(65) Arnold, L. D.; May, R. G.; Vederas, J. C. *J. Am. Chem. Soc.* 1988, 110, 2237.
(66) Reetz, M. T. *Angew. Chem., Int. Ed. Engl.* 1991, 30, 1531.
(67) Blaskovich, M. A.; Lajoie, G. A. *J. Am. Chem. Soc.* 1993, 115, 5021.

I claim:

1. A purified compound that predominately forms a single stereoisomer upon coordination to a metal center, the compound having the following formula I:

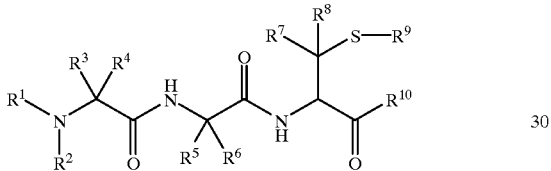
(I)

wherein $R^1$ is a linear or branched, saturated or unsaturated $C_{1-4}$alkyl chain that is optionally interrupted by one or two heteroatoms selected from N, O and S; and is optionally substituted by one or more substituents selected from halogen, hydroxyl, amino, carboxyl, $C_{1-4}$alkyl, aryl and $C(O)R^{10}$;

$R^2$ is H or a substituent defined by $R^1$;

$R^1$ and $R^2$ may together form a 5- to 8-membered saturated or unsaturated heterocyclic ring optionally substituted by one or more substituents selected from halogen, hydroxyl, amino, carboxyl, oxo, $C_{1-4}$alkyl, aryl and $C(O)R^{10}$;

$R^3$, $R^4$ and $R^5$ are selected independently from H; carboxyl; $C_{1-4}$alkyl; $C_{1-4}$alkyl substituted with a substituent selected from hydroxyl, amino, sulfhydryl, halogen, carboxyl, $C_{1-4}$alkoxycarbonyl and aminocarbonyl; an alpha carbon side chain of a D- or L-amino acid other than proline; and $C(O)R^{10}$;

$R^6$ is an optionally substituted 3- to 6-membered heterocylic or carbocyclic ring;

or $R^6$ is

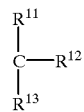

wherein $R^{11}$, $R^{12}$ and $R^{13}$ are independently selected from H, linear or branched, saturated or unsaturated $C_{1-6}$alkyl chain that is optionally interrupted by one or two heteroatoms selected from N, O and S; and is optionally substituted by one or more substituents selected from the group consisting of alkoxycarbonyl, aminocarbonyl, alkoxy, an optionally substituted 3- to 6-membered heterocylic and carbocyclic ring; with the proviso that at least one of $R^{11}$, $R^{12}$ and $R^{13}$ is not H;

or $R^6$ is

wherein $R^{14}$ and $R^{15}$ are independently selected from H, linear or branched, saturated or unsaturated $C_{1-6}$alkyl chain that is optionally interrupted by one or two heteroatoms selected from N, O and S; and is optionally substituted by one or more substituents selected from the group consisting of alkoxycarbonyl, aminocarbonyl, alkoxy, an optionally substituted 3- to 6-membered heterocylic and carbocyclic ring; with the proviso that at least one of $R^{14}$ and $R^{15}$ is not H;

or $R^6$ is

wherein X is selected from O or S and $R^{16}$ is selected from linear or branched, saturated or unsaturated $C_{1-6}$alkyl chain that is optionally interrupted by one or two heteroatoms selected from N, O and S; and is optionally substituted by one or more substituents selected from the group consisting of alkoxycarbonyl, aminocarbonyl, alkoxy, and an optionally substituted 3- to 6-membered heterocylic and carbocyclic ring;

$R^7$ and $R^8$ are selected independently from H; carboxyl; amino; $C_{1-4}$alkyl; $C_{1-4}$alkyl substituted by a substituent selected from hydroxyl, carboxyl and amino; and $C(O)R^{10}$;

$R^9$ is selected from H and a sulfur protecting group; and $R^{10}$ is selected from hydroxyl, alkoxy, an amino acid residue, a linking group and a targeting molecule.

2. A chirally pure compound that predominately forms a single stereoisomer upon coordination to a metal center of the formula II:

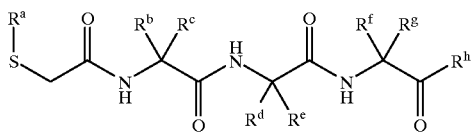
(II)

wherein
- $R^a$ is selected from H and a sulfur protecting group;
- $R^b$, $R^c$ $R^d$, $R^f$ and $R^g$ are selected independently from H; carboxyl; $C_{1-4}$alkyl; $C_{1-4}$alkyl substituted with a substituent selected from hydroxyl, amino, sulfhydryl, halogen, carboxyl, $C_{1-4}$alkoxycarbonyl and aminocarbonyl; an alpha carbon side chain of a D- or L-amino acid other than proline; and $C(O)R^h$;
- $R^e$ is an optionally subsituted 3- to 6-membered heterocylic or carbocylic ring;

or $R^e$ is

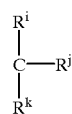

wherein $R^i$, $R^j$ and $R^k$ are independently selected from H, linear or branched, saturated or unsaturated $C_{1-6}$alkyl chain that is optionally interrupted by one or two heteroatoms selected from N, O and S; and is optionally substituted by one or more substituents; alkoxycarbonyl, aminocarbonyl, alkoxy, an optionally subsituted 3- to 6-membered heterocylic or carbocylic ring; with the proviso that a least one of $R^i$, $R^j$ and $R^k$ is not H;

or $R^e$ is

wherein $R^l$ and $R^m$ are independently selected from H, linear or branched, saturated or unsaturated $C_{1-6}$alkyl chain that is optionally interrupted by one or two heteroatoms selected from N, O and S; and is optionally substituted by one or more substituents; alkoxycarbonyl, aminocarbonyl, alkoxy, an optionally subsituted 3- to 6-membered heterocylic or carbocylic ring; with the proviso that a least one of $R^l$ and $R^m$ is not H;

or $R^e$ is

wherein X is selected from O or S and $R^n$ is selected from linear or branched, saturated or unsaturated $C_{1-6}$alkyl chain that is optionally interrupted by one or two heteroatoms selected from N, O and S; and is optionally substituted by one or more substituents; alkoxycarbonyl, aminocarbonyl, alkoxy, and an optionally subsituted 3- to 6-membered heterocylic or carbocylic ring; and $R^h$ is selected from hydroxyl, alkoxy, an amino acid residue, a linking group and a targeting molecule.

3. A chirally pure compound that predominately forms a single stereoisomer upon coordination to a metal center selected from:

Dimethylgly-L-t-Butylgly-L-Cys-Gly;
Dimethylgly-D-t-Butylgly-L-Cys-Gly;
Dimethylgly-L-t-Butylgly-L-Cys; and
Dimethylgly-L-t-Butylgly-L-Cys($S^e$-Acm)-Gly-Thr-Lys-Pro-Pro-Arg.

4. A compound according to any of claims 1 to 3 in a from complexed with a metal or metal radionuclide or an oxide or nitride thereof.

5. A pharmaceutical composition, comprising a pharmaceutically acceptable carrier and a compound as defined in claim 4 in an amount effective to image a site of diagnostic interest.

6. A method of radioimaging a site of diagnostic interest, comprising the step of administering systemically to a patient a pharmaceutical composition as defined in claim 5, allowing the pharmaceutical to localize within the site of diagnostic interest, and then taking an image of the patient so treated.

7. A compound according to claim 4 wherein the compound is in a form complexed with $^{99m}$Tc.

* * * * *

SEQUENCE LISTING

```
<160> NUMBER OF SEQ ID NOS: 12

<210> SEQ ID NO 1
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine.
<220> FEATURE:
<221> NAME/KEY: MOD_RES
<222> LOCATION: (2)
<223> OTHER INFORMATION: t-butyl glycine
<220> FEATURE:
<220> FEATURE:
<223> OTHER INFORMATION: Description of Artificial Sequence: Synthetic
      Peptide

<400> SEQUENCE: 1

Gly Gly Cys Gly
  1

<210> SEQ ID NO 2
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine.
<220> FEATURE:
<221> NAME/KEY: MOD_RES
<222> LOCATION: (2)
<223> OTHER INFORMATION: L-t-butylglycine.
<220> FEATURE:
<221> NAME/KEY: MOD_RES
<222> LOCATION: (3)
<223> OTHER INFORMATION: L-cysteine.
<220> FEATURE:
<220> FEATURE:
<223> OTHER INFORMATION: Description of Artificial Sequence: Synthetic
      Peptide

<400> SEQUENCE: 2

Gly Gly Cys Gly
  1

<210> SEQ ID NO 3
<211> LENGTH: 4
```

```
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine.
<220> FEATURE:
<221> NAME/KEY: MOD_RES
<222> LOCATION: (2)
<223> OTHER INFORMATION: D-t-butyl glycine.
<220> FEATURE:
<221> NAME/KEY: MOD_RES
<222> LOCATION: (3)
<223> OTHER INFORMATION: L-cysteine.
<220> FEATURE:
<220> FEATURE:
<223> OTHER INFORMATION: Description of Artificial Sequence: Synthetic
      Peptide

<400> SEQUENCE: 3

Gly Gly Cys Gly
  1

<210> SEQ ID NO 4
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine.
<220> FEATURE:
<221> NAME/KEY: MOD_RES
<222> LOCATION: (2)
<223> OTHER INFORMATION: L-Serine.
<220> FEATURE:
<221> NAME/KEY: MOD_RES
<222> LOCATION: (3)
<223> OTHER INFORMATION: L-cysteine.
<220> FEATURE:
<220> FEATURE:
<223> OTHER INFORMATION: Description of Artificial Sequence: Synthetic
      Peptide

<400> SEQUENCE: 4

Gly Ser Cys Gly
  1

<210> SEQ ID NO 5
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine.
<220> FEATURE:
<221> NAME/KEY: MOD_RES
<222> LOCATION: (2)
<223> OTHER INFORMATION: L-Isoleucine.
<220> FEATURE:
<221> NAME/KEY: MOD_RES
<222> LOCATION: (3)
<223> OTHER INFORMATION: L-Cysteine.
<220> FEATURE:
<220> FEATURE:
<223> OTHER INFORMATION: Description of Artificial Sequence: Synthetic
      Peptide

<400> SEQUENCE: 5

Gly Ile Cys Gly
  1
```

```
<210> SEQ ID NO 6
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine.
<220> FEATURE:
<220> FEATURE:
<223> OTHER INFORMATION: Description of Artificial Sequence: Synthetic
      Peptide

<400> SEQUENCE: 6

Gly Ser Cys Gly
  1

<210> SEQ ID NO 7
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: dimethylglycine
<220> FEATURE:
<221> NAME/KEY: MOD_RES
<222> LOCATION: (2)
<223> OTHER INFORMATION: L-isoleucine
<220> FEATURE:
<221> NAME/KEY: MOD_RES
<222> LOCATION: (3)
<223> OTHER INFORMATION: Acetoamidomethyl group is attached to the
      peptide chain via the atom, S, on the amino acid side chain.
<220> FEATURE:
<220> FEATURE:
<223> OTHER INFORMATION: Description of Artificial Sequence: Synthetic
      Peptide

<400> SEQUENCE: 7

Gly Ile Cys Gly
  1

<210> SEQ ID NO 8
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: dimethylglycine
<220> FEATURE:
<221> NAME/KEY: MOD_RES
<222> LOCATION: (2)
<223> OTHER INFORMATION: L-t-butylglycine
<220> FEATURE:
<221> NAME/KEY: MOD_RES
<222> LOCATION: (3)
<223> OTHER INFORMATION: L-cysteine with an acetoamidomethyl protecting
      group attached via the Sulfur atom.
<220> FEATURE:
<220> FEATURE:
<223> OTHER INFORMATION: Description of Artificial Sequence: Synthetic
      Peptide

<400> SEQUENCE: 8

Gly Gly Cys Gly
  1

<210> SEQ ID NO 9
<211> LENGTH: 4
<212> TYPE: PRT
<213> ORGANISM: Artificial Sequence
```

```
<220> FEATURE:
<221> NAME/KEY: MOD_RES
<222> LOCATION: (1)
<223> OTHER INFORMATION: Dimethylglycine.
<220> FEATURE:
<221> NAME/KEY: MOD_RES
<222> LOCATION: (2)
<223> OTHER INFORMATION: D-t-butylglycine.
<220> FEATURE:
<221> NAME/KEY: MOD_RES
<222> LOCATION: (3)
<223> OTHER INFORMATION: L-cysteine with an acetoamidomethyl protecting
      group attached via the Sulfur atom.
<220> FEATURE:
<220> FEATURE:
<223> OTHER INFORMATION: Description of Artificial Sequence: Synthetic
      Peptide

<400> SEQUENCE: 9

Gly Gly Cys Gly
  1

<210> SEQ ID NO 10
<211> LENGTH: 9
<212> TYPE: PRT
<213> ORGANISM: Artificial Sequence
<220> FEATURE:
<221> NAME/KEY: MOD_RES
<222> LOCATION: (1)
<223> OTHER INFORMATION: dimethylglycine
<220> FEATURE:
<221> NAME/KEY: MOD_RES
<222> LOCATION: (2)
<223> OTHER INFORMATION: L-t-butylglycine
<220> FEATURE:
<221> NAME/KEY: MOD_RES
<222> LOCATION: (3)
<223> OTHER INFORMATION: L-cysteine with an acetoamidomethyl protecting
      group attached via the Sulfur atom.
<220> FEATURE:
<220> FEATURE:
<223> OTHER INFORMATION: Description of Artificial Sequence: Synthetic
      Peptide

<400> SEQUENCE: 10

Gly Gly Cys Gly Thr Lys Pro Pro Arg
  1               5

<210> SEQ ID NO 11
<211> LENGTH: 9
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine.
<220> FEATURE:
<221> NAME/KEY: MOD_RES
<222> LOCATION: (2)
<223> OTHER INFORMATION: L-t-butyl glycine
<220> FEATURE:
<221> NAME/KEY: MOD_RES
<222> LOCATION: (3)
<223> OTHER INFORMATION: L-cysteine.
<220> FEATURE:
<223> OTHER INFORMATION: Description of Artificial Sequence: Synthetic
      Peptide

<400> SEQUENCE: 11

Gly Gly Cys Gly Thr Lys Pro Pro Arg
  1               5

<210> SEQ ID NO 12
```

```
-continued

<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Dimethylglycine.
<220> FEATURE:
<223> OTHER INFORMATION: Description of Artificial Sequence: Synthetic
      Peptide

<400> SEQUENCE: 12

Gly Ile Cys Gly
```